US00PP09367P

United States Patent [19]

Hope

[11] Patent Number: Plant 9,367

[45] Date of Patent: Nov. 7, 1995

[54] KALANCHOE PLANT NAMED 'PICO TICO CHERRY'

[75] Inventor: Claude Hope, Cartago, Costa Rica

[73] Assignee: Ball Seed Co., a Division of Geo. J. Ball, Inc., West Chicago, Ill.

[21] Appl. No.: 380,013

[22] Filed: Jan. 27, 1995

[51] Int. Cl.[6] ..... A01H 5/00

[52] U.S. Cl. ..... Plt./87.15

[58] Field of Search ..... Plt./87.15

*Primary Examiner*—James R. Feyrer
*Attorney, Agent, or Firm*—C. A. Whealy

[57] ABSTRACT

A distinct cultivar of Kalanchoe plant named Pico Tico Cherry, characterized by its very compact plant growth habit; freely branching habit; proportional leaf size; flowers that are borne just above the foliage; peduncles that do not stretch during flowering or during postproduction; cherry red flower color; and excellent keeping quality.

1 Drawing Sheet

The present invention relates to a new and distinctive cultivar of Kalanchoe plant, botanically known as *Kalanchoe blossfeldiana,* and hereinafter referred to by the cultivar name Pico Tico Cherry.

The new cultivar is a product of a planned breeding program conducted by the inventor in Cartago, Costa Rica.

The new cultivar originated from a cross made by the inventor of the proprietary selection K1RO 3722 as the male or pollen parent with the proprietary selection K1P 109-2-7-7 as the female or seed parent.

The cultivar Pico Tico Cherry was discovered and selected by the inventor as a following plant within the progeny of the stated cross in a controlled environment in Cartago, Costa Rica. Asexual reproduction of the new cultivar by terminal cuttings taken at Cartago, Costa Rica, and subsequently at West Chicago, Ill., has shown that the unique features of this new Kalanchoe are stabilized and reproduced true to type in successive generations of asexual reproduction.

The cultivar Pico Tico Cherry has not been observed under all possible environmental conditions. The phenotype may vary somewhat with variations in environment such as temperature, daylength and light intensity, without, however, any variance in genotype. The following observations, measurements and comparisons describe plants grown in West Chicago, Ill., under commercial practice in a glass-covered greenhouse.

The following traits have been repeatedly observed and are determined to be the unique characteristics of Pico Tico Cherry. These characteristics in combination distinguish Pico Tico Cherry as a new and distinct cultivar:

1. Very compact plant growth habit. Plants do not require plant growth retardants and can be produced in 8-cm or smaller containers.
2. Plants are freely branching and do not require pinching.
3. Leaf size is proportional to plant size.
4. Peduncles do not stretch during flowering or during postproduction.
5. Petals are cherry red in color.
6. Plants have excellent keeping quality. Flowers do not fade and foliage maintains good color for six weeks under interior conditions.
7. Flowers are borne just above the foliage giving plants a mounded appearance.

The new Kalanchoe differs from its parents in the color of the petals. The petal color of the male parent, K1RO 3722, is light pink; and the petal color of the female parent, selection K1P 109-2-7-7, is dark scarlet in contrast to the cherry red color of Pico Tico Cherry petals.

Pico Tico Cherry is most similar to the nonpatented Kalanchoe cultivar Tico Red Velvet in its flower and leaf colors, however it differs from Tico Red Velvet in the following characteristics:

1. Plants of Pico Tico Cherry are more compact in plant growth habit than plants of Tico Red Velvet.
2. Plants of Pico Tico Cherry are suitable for 8-cm or smaller containers, whereas plants of Tico Red Velvet are suitable for 10 to 12.5-cm containers.
3. Leaves of plants of Pico Tico Cherry are smaller than leaves of plants of Tico Red Velvet.
4. Main stem diameter of plants of Pico Tico Cherry is smaller compared to plants of Tico Red Velvet.
5. Plants of Pico Tico Cherry have fewer flowers per main cyme compared to plants of Tico Red Velvet.

The accompanying colored photograph illustrates the overall appearance of the new cultivar, showing the colors as true as it is reasonably possible to obtain in colored reproductions of this type. The photograph comprises a side perspective view of a typical potted plant of Pico Tico Cherry.

In the following description, color references are made to The Royal Horticultural Society Colour Chart except where general terms of ordinary dictionary significance are used. Measurements and numerical values represent averages for eight typical plants.

Botanical classification: *Kalanchoe blossfeldiana* cultivar Pico Ticho Cherry.

Parentage:

*Male.*—Proprietary selection K1RO 3722

*Female.*—Proprietary selection K1P 109-2-7-7

Propagation:

A. *Type cutting.*—Terminal tip cuttings.

B. *Time to initiate roots.*—7 days at 25° C. soil temperature.

C. *Rooting habit.*—Fine, fibrous, and well-branched.

Plant description:

A. *Form.*—Upright and moderately compact.

B. *Habit of growth.*—Freely branching.

C. *Plant height at flowering.*—12 cm.

D. *Foliage description.*—1. Size: a. Length: 8 cm. b. Width: 5 cm. 2. Shape: Ovate. 3. Texture: Succulent. 4. Margin: Crenate. 5. Color: a. Young foliage top side 147A. b. Young foliage under side: 147B. c. Mature foliage top side: 147A. d. Mature foliage under side: 147B. e. Leaf margin: 59A.

E. *Stem description.*—1. Main stem diameter: 0.7 cm. 2. Color: 147B.

Flower description:

A. *Flower type and habit.*—Freely flowering, flowers arranged in panicles, cymose.

B. *Natural flowering season.*—Autumn/winter in Northern Hemisphere. Flower initiation and development can be induced under short day/long night conditions.

C. *Flowers borne.*—Just above foliage, arising from leaf axils.

D. *Quantity of flowers.*—40 on lateral cymes, 40 on main cyme.

E. *Petals.*—1. Shape: Elliptic. 2. Base: Linear. 3. Tip: Acute. 4. Size: a. Length: 1.4 cm. b. Width: 0.8 cm. 5. Color: a. When opening: 57A. b. Mature, top side: 57A. c. Mature, under side: 57D. d. Fading to: 57A. e. Peduncle: 147B.

F. *Reproductive organs.*—1. Stamens: a. Stamen number: 8. b. Anther color: 143B. c. Pollen color: 5B. 2. Pistils: a. Stigma color: 3C. b. Style color: 143B. c. Ovary number: 4. d. Ovary size: (1) Length: 4 mm. (2) Width: 1 mm. e. Ovary color: 143B.

Disease resistance: No fungal, bacterial nor viral problems observed.

Seed production: Seed production has not been observed.

I claim:

1. A new and distinct cultivar of Kalanchoe plant named Pico Tico Cherry, as illustrated and described.

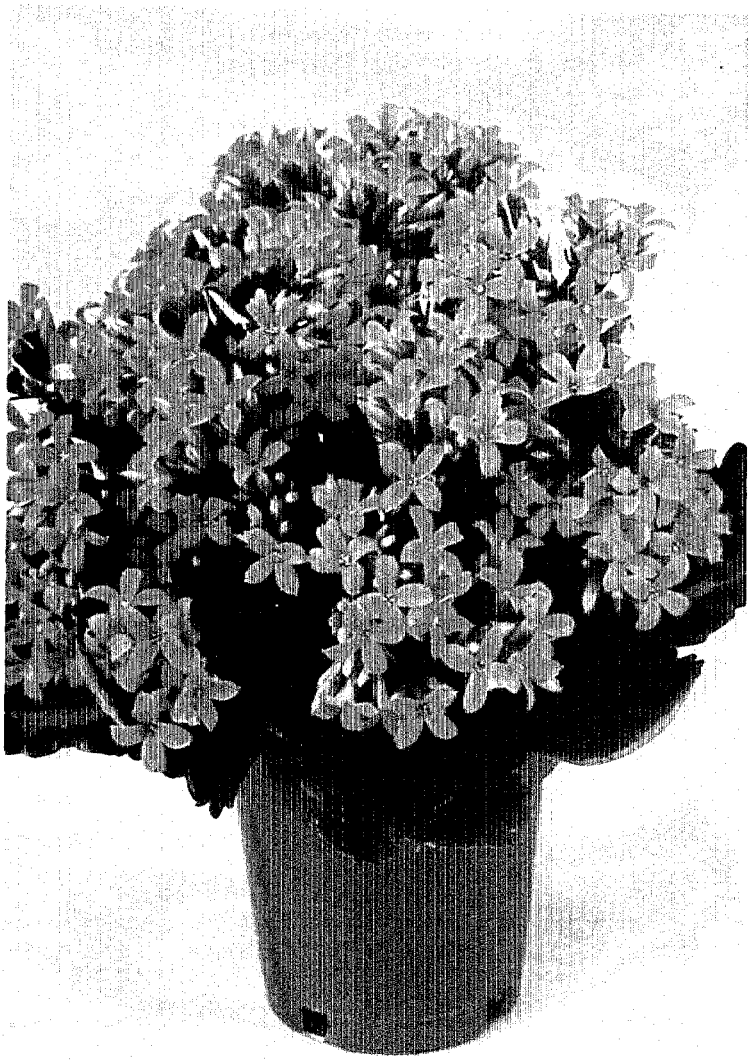

* * * * *